US012583891B2

(12) United States Patent
Vander Elst et al.

(10) Patent No.: US 12,583,891 B2
(45) Date of Patent: *Mar. 24, 2026

(54) PEPTIDES AND METHODS FOR THE TREATMENT OF DIABETES

(71) Applicant: IMCYSE SA, Liège (BE)

(72) Inventors: Luc Vander Elst, Obaix (BE); Vincent Carlier, Enines (BE); Jean-Marie Saint-Remy, Grez-Doiceau (BE)

(73) Assignee: PHOENIX ALPHA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,172

(22) Filed: Aug. 8, 2023

(65) Prior Publication Data

US 2024/0092843 A1     Mar. 21, 2024

Related U.S. Application Data

(60) Continuation of application No. 17/854,190, filed on Jun. 30, 2022, now Pat. No. 11,760,782, which is a division of application No. 17/019,695, filed on Sep. 14, 2020, now Pat. No. 11,407,795, which is a division of application No. 16/531,276, filed on Aug. 5, 2019, now Pat. No. 10,808,016, which is a continuation of application No. PCT/EP2018/055501, filed on Mar. 6, 2018.

(30) Foreign Application Priority Data

Mar. 9, 2017     (EP) ..................................... 17160085

(51) Int. Cl.
| | |
|---|---|
| C07K 14/435 | (2006.01) |
| A61K 35/17 | (2025.01) |
| A61P 3/10 | (2006.01) |
| C07K 7/08 | (2006.01) |
| C12N 5/0783 | (2010.01) |
| A61K 38/00 | (2006.01) |

(52) U.S. Cl.
CPC ............ C07K 14/435 (2013.01); A61K 35/17 (2013.01); A61P 3/10 (2018.01); C07K 7/08 (2013.01); C12N 5/0636 (2013.01); *A61K 38/00* (2013.01)

(58) Field of Classification Search
CPC .......... C07K 14/435; A61P 3/10; A61K 35/17
See application file for complete search history.

(56) References Cited

U.S. PATENT DOCUMENTS

| | | | |
|---|---|---|---|
| 8,999,346 B2 | 4/2015 | Saint-Remy |
| 9,044,507 B2 | 6/2015 | Saint-Remy |
| 9,248,171 B2 | 2/2016 | Saint-Remy |
| 9,249,202 B2 | 2/2016 | Saint-Remy |
| 9,394,517 B2 | 7/2016 | Saint-Remy |
| 9,861,661 B2 | 1/2018 | Saint-Remy |
| 10,023,847 B2 | 7/2018 | Saint-Remy | |
| 10,617,748 B2 | 4/2020 | Saint-Remy | |
| 10,662,232 B2 | 5/2020 | Saint-Remy | |
| 10,729,791 B2 | 8/2020 | Saint-Remy | |
| 10,808,016 B2 * | 10/2020 | Vander Elst | .............. A61P 3/10 |
| 10,899,795 B2 | 1/2021 | Saint-Remy | |
| 10,982,196 B2 | 4/2021 | Saint-Remy | |
| 11,193,114 B2 | 12/2021 | Saint-Remy | |
| 11,226,332 B2 | 1/2022 | Saint-Remy | |
| 11,407,795 B2 * | 8/2022 | Vander Elst | ............ C07K 7/08 |
| 11,485,768 B2 | 11/2022 | Vander Elst | |
| 11,718,650 B2 | 8/2023 | Saint-Remy | |
| 11,760,782 B2 * | 9/2023 | Vander Elst | ........... C07K 14/62 |
| | | | 514/7.3 |
| 11,787,849 B2 | 10/2023 | Saint-Remy | |
| 12,023,384 B2 | 7/2024 | Saint-Remy et al. | |
| 2010/0303866 A1 | 12/2010 | Saint-Remy | |
| 2010/0330088 A1 | 12/2010 | Saint-Remy | |
| 2011/0111395 A1 | 5/2011 | Saint-Remy | |
| 2012/0009678 A1 | 1/2012 | Saint-Remy | |
| 2014/0186297 A1 | 7/2014 | Saint-Remy | |
| 2014/0370044 A1 | 12/2014 | Saint-Remy | |
| 2014/0377299 A1 | 12/2014 | Saint-Remy | |
| 2015/0110821 A1 | 4/2015 | Saint-Remy | |
| 2015/0125536 A1 | 5/2015 | Santamaria | |
| 2016/0091492 A1 | 3/2016 | Saint-Remy | |
| 2016/0108103 A1 | 4/2016 | Saint-Remy | |
| 2016/0194367 A1 | 7/2016 | Saint-Remy | |
| 2017/0100466 A1 | 4/2017 | Saint-Remy | |
| 2018/0228912 A1 | 8/2018 | Saint-Remy | |
| 2018/0258154 A1 | 9/2018 | Saint-Remy | |
| 2019/0352348 A1 | 11/2019 | Vander Elst | |
| 2020/0179499 A1 | 6/2020 | Saint-Remy | |
| 2020/0270331 A1 | 8/2020 | Saint-Remy | |
| 2020/0397911 A1 | 12/2020 | Saint-Remy | |
| 2020/0407406 A1 | 12/2020 | Vander Elst | |

(Continued)

FOREIGN PATENT DOCUMENTS

| | | |
|---|---|---|
| WO | 2008/017517 | 2/2008 |
| WO | 2009101204 | 8/2009 |

(Continued)

OTHER PUBLICATIONS

U.S. Appl. No. 18/563,288, filed Nov. 21, 2023.
International Search Report for PCT/EP2018/055501 mailed May 4, 2018, 5 pages.
Written Opinion for PCT/EP2018/055501 mailed May 4, 2018, 6 pages.
Database Geneseq [Online], "Human preproinsulin (PPI) antigenic peptide, SEQ ID 164", Jan. 26, 2017, 2 pages.
Abrahimians et al., "MHC Class II-Restricted Epitopes Containing an Oxidoreductase Activity Prompt CD4(+) T Cells with Apoptosis-Inducing Properties", Frontiers in Immunology, vol. 6, Sep. 1, 2015, Article 449, 5 pages.
Abrahimians et al., "Thioreductase-Containing Epitopes Inhibit the Development of Type I Diabetes in the NOD Mouse Model", Frontiers in Immunology, vol. 7, Mar. 2, 2016.

(Continued)

*Primary Examiner* — Amber D Steele
(74) *Attorney, Agent, or Firm* — Nixon & Vanderhye, PC

(57) ABSTRACT
The invention relates to peptides such as HCPYCSLQPLA-LEGSLQKRG [SEQ ID NO: 26] and their use in the treatment of type 1 diabetes and the generation of cytolytic CD4+ T cell.

11 Claims, 2 Drawing Sheets

Specification includes a Sequence Listing.

(56) References Cited

U.S. PATENT DOCUMENTS

| | | |
|---|---|---|
| 2021/0188913 A1 | 6/2021 | Saint-Remy |
| 2021/0401976 A1 | 12/2021 | Erak |
| 2022/0119778 A1 | 4/2022 | Saint-Remy |
| 2022/0288179 A1 | 9/2022 | Erak |
| 2022/0411476 A1 | 12/2022 | Vander Elst |
| 2023/0113747 A1 | 4/2023 | Erak |
| 2023/0136112 A1 | 5/2023 | Carlier |
| 2023/0172894 A1 | 6/2023 | Saint-Remy |
| 2023/0181638 A1 | 6/2023 | Erak |
| 2023/0265156 A1 | 8/2023 | Vander Elst |
| 2023/0340061 A1 | 10/2023 | Saint-Remy |
| 2024/0034759 A1 | 2/2024 | Saint-Remy |
| 2024/0109951 A1 | 4/2024 | Saint-Remy |
| 2024/0132556 A1 | 4/2024 | Erak |
| 2024/0158464 A1 | 5/2024 | Saint-Remy |
| 2024/0189404 A1 | 6/2024 | Erak |
| 2024/0207379 A1 | 6/2024 | Saint-Remy |
| 2024/0285737 A1 | 8/2024 | Van Rampelbergh |

FOREIGN PATENT DOCUMENTS

| | | | |
|---|---|---|---|
| WO | 2011120994 | 10/2011 | |
| WO | 2013113076 | 8/2013 | |
| WO | 2014/191432 | 12/2014 | |
| WO | 2015063616 | 5/2015 | |
| WO | 2016/059236 | 4/2016 | |
| WO | WO-2016059236 A1 * | 4/2016 | ....... C07K 14/70539 |

OTHER PUBLICATIONS

Brinster et al., "Costimulatory effects of IL-1 on the expansion/differentiation of CD4(+) CD25(+) Foxp3(+) and CD4(+) CD25(+) Foxp3(−) T cells", Journal of Leukocyte Biology, Federation of American Societies for Experimental Biology, vol. 84, No. 2, Aug. 1, 2008, pp. 480-487.

Terpe, 2003, Overview of tag protein fusions: from molecular fusions: from molecular and biochemical fundamentals to commercial systems, Appl. Micorbiol. Biotechnol., 60: 523:533.

Cong et al., 2012, Site-Specific PEGylation at Histidine Tags, Bioconjugate Chemistry, 23(2):248-263.

Galdiero et al., 2010, The Presence of a Single N-Terminal Histidine Residue Enhances the Fusogenic Properties of a Membranotropic Peptide Derived from Herpes Simplex Virus Type 1 Glycoprotein H, The Journal of Biological Chemistry, 285(22):17123-17136.

Muller, S., et al., "Spliceosomal Peptide P140 for Immunotherapy of Systemic Lupus Erythematosus: Results of Early Phase II Clinical Trial," Arthritis & Rheumatism: Official Journal of the American College of Rheumatology, 2008, vol. 58, No. 12, pp. 3873-3883.

Anez, G., et al., "Passage of Dengue Virus Type 4 Vaccine Candidates in Fetal Rhesus Lung Cells Selects Heparin-Sensitive Variants That Result in Loss of Infectivity and Immunogenicity in Rhesus Macaques," Journal of Virology, 2009, vol. 83, No. 20, pp. 10384-10394.

Yarilin, A.A., "Fundamentals of Immunology," Moscow, Meditsina Publishers, 1999, pp. 221-223 and 228; in the Russian language with an English-language translation of the office action mailed in corresponding RU Appl. No. 2019126232 which references Yarilin A.A. at p. 5.

Laptev, D.N., "Immunotherapy for Type I Diabetes: State-of-Art and Prospects. Part 1," Probl. Endokrinol (Mosk), Aug. 15, 2009, vol. 55, No. 4, pp. 24-34; in the Russian language with an English language Abstract.

Carlier et al., Increased Synapse Formation Obtained by T cell Epitopes Containing a CxxC Motif in Flanking Residues Convert CD4+ T Cells into Cytolytic Effectors, PLOS One, 2012, 7(10):e45366.

Fomenko, D.E. and Gladyshev, V.N., Identity and Functions of Cxxc-derived Motifs, Biochemistry, 2003, 42(38):11214-11225.

Kortemme, T et al., Electrostatic Interactions in the Active Site of the N-Terminal Thioredoxin-like Domain of Protein Disulfide Isomerase, Biochemistry, 1996, 35, 46, 14503-14511.

U.S. Appl. No. 18/332,985, filed Jun. 12, 2023, Saint-Remy, related application.

U.S. Appl. No. 18/342,897, filed Jun. 28, 2023, Saint-Remy, related application.

U.S. Appl. No. 17/934,607, filed Sep. 23, 2022, Vander Elst, related application.

U.S. Appl. No. 17/923,108, filed Nov. 3, 2022, Saint-Remy, related application.

U.S. Appl. No. 17/923,177, filed Nov. 3, 2022, Erak, related application.

U.S. Appl. No. 17/923,217, filed Nov. 3, 2022, Erak, related application.

* cited by examiner

PEPTIDES AND METHODS FOR THE TREATMENT OF DIABETES

CROSS-REFERENCE TO RELATED APPLICATION

This application is a continuation of U.S. application Ser. No. 17/854,190, filed Jun. 30, 2022, now U.S. Pat. No. 11,760,782, issued Sep. 19, 2023, which is a divisional of U.S. application Ser. No. 17/019,695, filed Sep. 14, 2020, now U.S. Pat. No. 11,407,795, issued on Aug. 9, 2022, which is a divisional of U.S. application Ser. No. 16/531, 276, 371 (c) date Aug. 5, 2019, now U.S. Pat. No. 10,808, 016, issued Oct. 20, 2020, which is a continuation of International Application No. PCT/EP2018/055501 filed Mar. 6, 2018 which designated the U.S. and claims priority to EP patent application Ser. No. 17/160,085.1 filed Mar. 9, 2017, the entire contents of each of which are hereby incorporated by reference.

REFERENCE TO A SEQUENCE LISTING SUBMITTED ELECTRONICALLY VIA EFS-WEB

The content of the electronically submitted sequence listing (Name: 2752_0145_Sequence_Listing.xml, Size: 31,954 bytes; and Date of Creation: Nov. 27, 2023) is herein incorporated by reference in its entirety.

BACKGROUND OF THE INVENTION

Several strategies have been described to prevent the generation of an unwanted immune response against an antigen. WO2008/017517 describes a new strategy using peptides comprising an MHC class II antigen of a given antigenic protein and an oxidoreductase motif. These peptides convert CD4+ T cells into a cell type with cytolytic properties called cytolytic CD4+ T cells. These cells are capable to kill via triggering apoptosis those antigen presenting cells (APC), which present the antigen from which the peptide is derived. WO2008/017517 demonstrates this concept for allergies and auto-immune diseases such as type I diabetes. Herein insulin can act as an auto-antigen.

WO2009101207 and Carlier et al. (2012) *Plos one* 7, e45366 further describe the antigen specific cytolytic cells in more detail.

WO2009101206 describes the use of peptides with an oxidoreductase motif and an MCH class II epitope of a soluble allo-antigen to prevent an immune response against such antigen when used in replacement therapies (e.g. unwanted immune response against injected insulin in diabetes patents).

WO2016059236 discloses further modified peptides wherein an additional Histidine is present in the proximity of the oxidoreductase motif.

In the design of a peptide against type I diabetes, many factors can be taken into account, such as the type of the auto-antigen (insulin, GAD 65, . . . ), a specific domain and epitope of the auto-antigen, the oxidoreductase motif, the length and amino-acid acid sequence between the oxidoreductase motif and the epitope sequence.

SUMMARY OF THE INVENTION

The present invention provides novel peptides derived from Insulin for the treatment of type 1 diabetes.

The peptides of the present invention have the advantage that cytolytic CD4+ T cells which have been generated using these peptides have an increased IFN-gamma and sFasL production compared to prior art peptides. Also Granzyme B production in said CD4+ T cells is believed to be increased.

The increased expression levels of these markers are indications of a greater capacity of the peptides of the present invention to generate cytolytic CD4+ T cells compared to the prior art peptides.

One aspect of the invention relates to peptides with a length of between 12 and 50 amino acids, comprising the tetrapeptide sequence Cxx[CST] [SEQ ID NO: 1] or [CST] xxC [SEQ ID NO: 2] (i.e. the redox motif) and, separated from this tetrapeptide by 0 to 5 amino acids, preferably by 0 to 4 amino acids (i.e. by a linker), the sequence LALEGSLQK [SEQ ID NO: 3] (i.e. the epitope).

Embodiments of these peptides comprise the sequence Cxx[CST]SLQPLALEGSLQK [SEQ ID NO: 4] or [CST] xxCSLQPLALEGSLQK [SEQ ID NO:5].

Other embodiments of these peptides comprise the sequence CxxCSLQPLALEGSLQK [SEQ ID NO: 6].

Other embodiments of these peptides comprise the sequence

```
                                         [SEQ ID NO: 7]
        HCxx[CST]SLQPLALEGSLQK
        or
                                         [SEQ ID NO: 8]
        H[CST]xxCSLQPLALEGSLQK.
```

Other embodiments of these peptides comprise the sequence

```
                                         [SEQ ID NO: 9]
             HCxxCSLQPLALEGSLQK
```

Other embodiments of these peptides comprise the Cxx [CST] [SEQ ID NO: 1] or [CST]xxC [SEQ ID NO: 2] redox motif sequence and the sequence

```
                                        [SEQ ID NO: 20]
                 SLQPLALEGSLQKRG.
```

Specific embodiments of these peptides consist of the sequence

```
                                         [SEQ ID NO: 4]
             Cxx[CST]SLQPLALEGSLQK,

[SEQ ID NO: 5]
             [CST]xxCSLQPLALEGSLQK,

[SEQ ID NO: 6]
             CxxCSLQPLALEGSLQK,

[SEQ ID NO: 7]
             HCxx[CST]SLQPLALEGSLQK,

[SEQ ID NO: 8]
             H[CST]xxCSLQPLALEGSLQK,
             or
                                         [SEQ ID NO: 9]
             HCxxCSLQPLALEGSLQK.
```

Other specific embodiments of these peptides consist of the sequence

```
                                        [SEQ ID NO: 10]
    Cxx[CST]SLQPLALEGSLQKRG,

[SEQ ID NO: 11]
    [CST]xxCSLQPLALEGSLQKRG,

[SEQ ID NO: 12]
    CxxCSLQPLALEGSLQKRG,

[SEQ ID NO: 13]
    HCxx[CST]SLQPLALEGSLQKRG,

[SEQ ID NO: 14]
    H[CST]xxCSLQPLALEGSLQKRG,
    or

[SEQ ID NO: 15]
    HCxxCSLQPLALEGSLQKRG.
```

In specific embodiments of these sequences Cxx[CST] [SEQ ID NO: 1] is CPY[CST] [SEQ ID NO: 16], [CST]xxC [SEQ ID NO: 2] is [CST]PYC [SEQ ID NO: 17], more specific CxxC [SEQ ID NO: 18] is CPYC [SEQ ID NO:19].

A specific embodiment is the peptide HCPYCSLQPLA-LEGSLQKRG [SEQ ID NO: 26]

In the above embodiments the redox motif is at the N terminal side of the epitope.

In an alternative set of embodiments the peptides have the redox motif at the C terminal side of the epitope.

Another aspect of the invention relates to any one of the peptides as disclosed above for use as a medicament, especially in the treatment or prevention of type 1 diabetes or for reducing the symptoms of type 1 diabetes.

Another aspect relates to pharmaceutical compositions comprising any one of the peptides as disclosed above and a pharmaceutically acceptable carrier.

Another aspect relates to an in vitro method for the generation of a population of cytolytic CD4+ T cells, against APC presenting insulin epitopes, comprising the steps of:

providing peripheral blood cells;

contacting said cells in vitro with any one of the immunogenic peptides as disclosed above; and expanding said cells in the presence of IL-2.

Another aspect relates to a population of cells cytolytic CD4+ T cells, against insulin presenting APC obtainable by the above method for use as a medicament.

Another aspect relates to a population of cells obtainable by the above method for use in the treatment or prevention of type 1 diabetes.

DETAILED DESCRIPTION OF THE INVENTION

Figure 1:
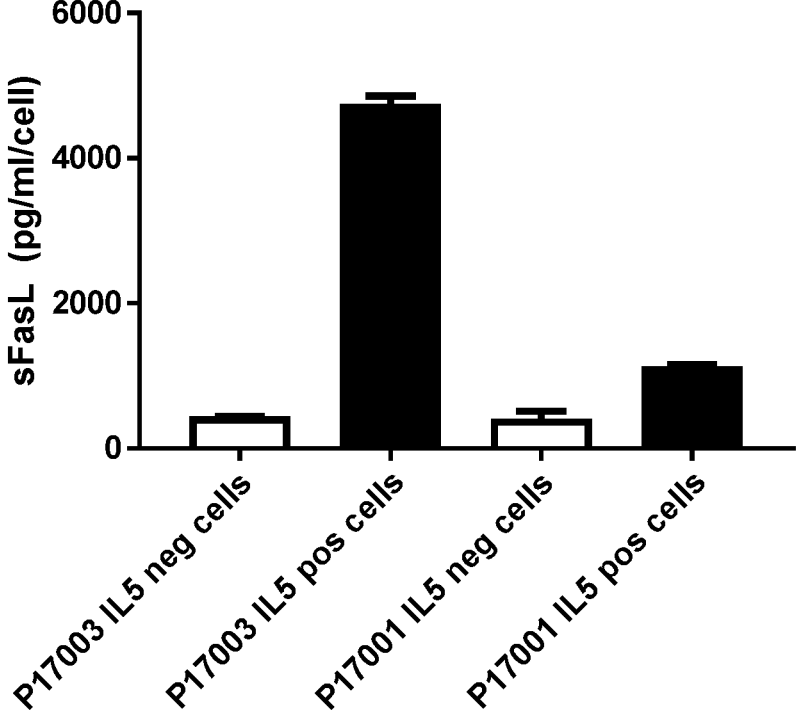
FIG. 1: Release of sFasL in cell lines generated with p17-003 or p17-001. Cells specific for p17-003 or p17-001 (IL5 positive cells; black histograms) were restimulated for 24 h with antigen presenting cells loaded with peptides p17-003 or p17-001, depending of the peptide used for their generation, and supernatant collected after 24 h of co-culture. IL-5 negative cells are for control PBMC populations (open histograms). Results represent mean+/−SD of sFasL concentration corrected per cell number.

The present invention will be described with respect to particular embodiments but the invention is not limited thereto but only by the claims. Any reference signs in the claims shall not be construed as limiting the scope. The following terms or definitions are provided solely to aid in the understanding of the invention. Unless specifically defined herein, all terms used herein have the same meaning as they would to one skilled in the art of the present invention. The definitions provided herein should not be construed to have a scope less than the one understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the singular forms 'a', 'an', and 'the' include both singular and plural referents unless the context clearly dictates otherwise. The term "any" when used in relation to aspects, claims or embodiments as used herein refers to any single one (i.e. anyone) as well as to all combinations of said aspects, claims or embodiments referred to.

The terms 'comprising', 'comprises' and 'comprised of' as used herein are synonymous with 'including', 'includes' or 'containing', 'contains', and are inclusive or open-ended and do not exclude additional, non-recited members, elements or method steps. Said terms also encompass the embodiments "consisting essentially of" and "consisting of".

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

As used herein, the term "for use" as used in "composition for use in treatment of a disease" shall disclose also the corresponding method of treatment and the corresponding use of a preparation for the manufacture of a medicament for the treatment of a disease".

The term "peptide" as used herein refers to a molecule comprising an amino acid sequence of between 12 and 200 amino acids, connected by peptide bonds, but which can comprise non-amino acid structures.

Peptides according to the invention can contain any of the conventional 20 amino acids or modified versions thereof, or can contain non-naturally occurring amino-acids incorporated by chemical peptide synthesis or by chemical or enzymatic modification.

The term "antigen" as used herein refers to a structure of a macromolecule, typically protein (with or without polysaccharides) or made of proteic composition comprising one or more hapten (s) and comprising T cell epitopes.

The term "antigenic protein" as used herein refers to a protein comprising one or more T cell epitopes. An auto-antigen or auto-antigenic protein as used herein refers to a human or animal protein present in the body, which elicits an immune response within the same human or animal body.

The term "epitope" refers to one or several portions (which may define a conformational epitope) of an antigenic protein which is/are specifically recognised and bound by an antibody or a portion thereof (Fab', Fab2', etc.) or a receptor presented at the cell surface of a B or T cell lymphocyte, and which is able, by said binding, to induce an immune response.

The term "T cell epitope" in the context of the present invention refers to a dominant, sub-dominant or minor T cell epitope, i.e. a part of an antigenic protein that is specifically recognised and bound by a receptor at the cell surface of a T lymphocyte. Whether an epitope is dominant, sub-domi-nant or minor depends on the immune reaction elicited against the epitope. Dominance depends on the frequency at which such epitopes are recognised by T cells and able to activate them, among all the possible T cell epitopes of a protein.

The T cell epitope is an epitope recognised by MHC class II molecules, which consists of a sequence of +/−9 amino acids which fit in the groove of the MHC II molecule. Within a peptide sequence representing a T cell epitope, the amino acids in the epitope are numbered P1 to P9, amino acids N-terminal of the epitope are numbered P−1, P−2 and so on, amino acids C terminal of the epitope are numbered P+1, P+2 and so on. Peptides recognised by MHC class II molecules and not by MHC class I molecules are referred to as MHC class II restricted T cell epitopes.

The term "MHC" refers to "major histocompatibility antigen". In humans, the MHC genes are known as HLA ("human leukocyte antigen") genes. Although there is no consistently followed convention, some literature uses HLA to refer to HLA protein molecules, and MHC to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLAs DQB1, HLA-DRA, and HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells.

Peptide fragments presented in the context of class I MHC molecules are recognised by CD8+ T lymphocytes (cytolytic T lymphocytes or CTLs). CD8+ T lymphocytes frequently mature into cytolytic effectors which can lyse cells bearing the stimulating antigen. Class II MHC molecules are expressed primarily on activated lymphocytes and antigen-presenting cells. CD4+ T lymphocytes (helper T lympho-cytes or Th) are activated with recognition of a unique peptide fragment presented by a class II MHC molecule, usually found on an antigen-presenting cell like a macro-phage or dendritic cell. CD4+T lymphocytes proliferate and secrete cytokines such as IL-2, IFN-gamma and IL-4 that support antibody mediated and cell mediated responses.

Functional HLAs are characterised by a deep binding groove to which endogenous as well as foreign, potentially antigenic peptides bind. The groove is further characterised by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8, 9 or 10 residues. However, it has been demonstrated that peptides of up to 12 amino acid residues are also capable of binding HLA class I. Comparison of the structures of different HLA complexes confirmed a general mode of binding wherein peptides adopt a relatively linear, extended conformation, or can involve central residues to bulge out of the groove.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form dif-ferent complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/−9 amino acids (i.e. 8, 9 or 10) of an MHC class II T cell epitope that fit in the groove of the MHC II molecule are usually numbered P1 to P9. Additional amino acids N-terminal of the epitope are numbered P−1, P−2 and so on, amino acids C-terminal of the epitope are numbered P+1, P+2 and so on.

The term "homologue" as used herein with reference to the epitopes used in the context of the invention, refers to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell. Particular homologues of an epitope correspond to the natural epitope modified in at most three, more particularly in at most 2, most particularly in one amino acid.

The term "derivative" as used herein with reference to the peptides of the invention refers to molecules which contain at least the peptide active portion (i.e. the redox motif and the MHC class II epitope capable of eliciting cytolytic CD4+ T cell activity) and, in addition thereto comprises a comple-mentary portion which can have different purposes such as stabilising the peptides or altering the pharmacokinetic or pharmacodynamic properties of the peptide.

The term "sequence identity" of two sequences as used herein relates to the number of positions with identical nucleotides or amino acids divided by the number of nucleo-tides or amino acids in the shorter of the sequences, when the two sequences are aligned. In particular, the sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" as used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. The nucleic acid encoding a peptide according to the invention or fragment thereof is a sequence encoding the peptide or fragment thereof originating from a mammal or corresponding to a mammalian, most particularly a human peptide fragment.

The term "immune disorders" or "immune diseases" refers to diseases wherein a reaction of the immune system is responsible for or sustains a malfunction or non-physiological situation in an organism. Included in immune disorders are, inter alia, allergic disorders and autoimmune diseases.

The terms "autoimmune disease" or "autoimmune disorder" refer to diseases that result from an aberrant immune response of an organism against its own cells and tissues due to a failure of the organism to recognise its own constituent parts (down to the sub-molecular level) as "self". The group of diseases can be divided in two categories, organ-specific and systemic diseases. An "allergen" is defined as a substance, usually a macromolecule or a proteic composition which elicits the production of IgE antibodies in predisposed, particularly genetically disposed, individuals (atopics) patients. Similar definitions are presented in Liebers et al. (1996) *Clin. Exp. Allergy* 26, 494-516.

The term "type 1 diabetes" (T1D) or "diabetes type 1" (also known as "type 1 diabetes mellitus" or "immune mediated diabetes" or formerly known as "juvenile onset diabetes" or "insulin dependent diabetes") is an autoimmune disorder that typically develops in susceptible individuals during childhood. At the basis of T1D pathogenesis is the destruction of most insulin-producing pancreatic beta-cells by an autoimmune mechanism. In short, the organism loses the immune tolerance towards the pancreatic beta-cells in charge of insulin production and induces an immune response, mainly cell-mediated, associated to the production of autoantibodies, which leads to the self-destruction of beta-cells.

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. Typically, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when referring to a peptide relates to the fact that the sequence is identical to a fragment of a naturally occurring protein (wild type or mutant). In contrast therewith the term "artificial" refers to a sequence which as such does not occur in nature. An artificial sequence is obtained from a natural sequence by limited modifications such as changing/deleting/inserting one or more amino acids within the naturally occurring sequence or by adding/removing amino acids N- or C-terminally of a naturally occurring sequence.

Amino acids are referred to herein with their full name, their three-letter abbreviation or their one letter abbreviation.

Motifs of amino acid sequences are written herein according to the format of Prosite. Motifs are used to describe a certain sequence variety at specific parts of a sequence. The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are optionally separated from each other by a hyphen (-). Repetition of an identical element within a motif can be indicated by placing behind that element a numerical value or a numerical range between parentheses. For example X(2) corresponds to X-X or XX; X(2, 5) corresponds to 2, 3, 4 or 5 X amino acids, A(3) corresponds to A-A-A or AAA.

To distinguish between the amino acids X, those between H and C are called external amino acids X (single underlined in the above sequence), those within the redox motif are called internal amino acids X (double underlined in the above sequence).

X represents any amino acid, particularly an L-amino acid, more particularly one of the 20 naturally occurring L-amino acids.

A peptide, comprising a T cell epitope and a modified peptide motif sequence, having reducing activity is capable of generating a population of antigen-specific cytolytic CD4+ T cell towards antigen-presenting cells.

Accordingly, in its broadest sense, the invention relates to peptides which comprise at least one T-cell epitope of an antigen (self or non-self) with a potential to trigger an immune reaction, and a modified thioreductase sequence motif with a reducing activity on peptide disulfide bonds. The T cell epitope and the modified redox motif sequence may be immediately adjacent to each other in the peptide or optionally separated by a one or more amino acids (so called linker sequence). Optionally the peptide additionally comprises an endosome targeting sequence and/or additional "flanking" sequences.

The peptides of the invention comprise an MHC class II T-cell epitope of an antigen (self or non self) with a potential to trigger an immune reaction, and a modified redox motif. The reducing activity of the motif sequence in the peptide can be assayed for its ability to reduce a sulfhydryl group such as in the insulin solubility assay wherein the solubility of insulin is altered upon reduction, or with a fluorescence-labelled substrate such as insulin. An example of such assay uses a fluorescent peptide and is described in Tomazzolli et al. (2006) *Anal. Biochem.* 350, 105-112. Two peptides with a FITC label become self-quenching when they covalently attached to each other via a disulfide bridge. Upon reduction by a peptide in accordance with the present invention, the reduced individual peptides become fluorescent again.

The modified redox motif may be positioned at the amino-terminus side of the T-cell epitope or at the carboxy-terminus of the T-cell epitope.

Peptide fragments with reducing activity are encountered in thioreductases which are small disulfide reducing enzymes including glutaredoxins, nucleoredoxins, thioredoxins and other thiol/disulfide oxidoreductases (Holmgren (2000) *Antioxid. Redox Signal.* 2, 811-820; Jacquot et al. (2002) *Biochem. Pharm.* 64, 1065-1069). They are multi-functional, ubiquitous and found in many prokaryotes and eukaryotes. They exert reducing activity for disulfide bonds on proteins (such as enzymes) through redox active cysteines within conserved active domain consensus sequences: CXXC [SEQ ID NO:18], CXXS [SEQ ID NO:23], CXXT [SEQ ID NO:24], SXXC [SEQ ID NO:21], TXXC [SEQ ID NO:22] (Fomenko et al. (2003) *Biochemistry* 42, 11214-11225; Fomenko et al. (2002) *Prot. Science* 11, 2285-2296), in which X stands for any amino acid. Such domains are also found in larger proteins such as protein disulfide isomerase (PDI) and phosphoinositide-specific phospholipase C.

The 4 amino acid redox motif as known from e.g. Fomenko and WO2008/017517 comprises a cysteine at position 1 and/or 4; thus the motif is either CXX[CST] [SEQ ID NO: 1] or [CST]XXC [SEQ ID NO:2]. Such a tetrapeptide sequence will be referred to as "the motif". The motif in a peptide can be any of the alternatives CXXC [SEQ ID NO:18], SXXC [SEQ ID NO:21], TXXC [SEQ ID NO:22], CXXS [SEQ ID NO:23] or CXXT [SEQ ID NO:24]. In particular, peptides contain the sequence motif CXXC [SEQ ID NO:18].

As explained in detail further on, the peptides of the present invention can be made by chemical synthesis, which allows the incorporation of non-natural amino acids. Accordingly, "C" in the above recited redox modified redox motifs represents either cysteine or another amino acid with a thiol group such as mercaptovaline, homocysteine or other natural or non-natural amino acids with a thiol function. In order to have reducing activity, the cysteines present in a modified redox motif should not occur as part of a cystine disulfide bridge. Nevertheless, a redox modified redox motif may comprise modified cysteines such as methylated cysteine, which is converted into cysteine with free thiol groups in vivo. X can be any of the 20 natural amino acids, including S, C, or T or can be a non-natural amino acid. In particular embodiments X is an amino acid with a small side chain such as Gly, Ala, Ser or Thr. In further particular embodiments, X is not an amino acid with a bulky side chain such as Trp. In further particular embodiments X is not Cysteine. In further particular embodiments at least one X in the modified redox motif is His. In other further particular embodiments at least one X in the modified redox is Pro.

Peptides may further comprise modifications to increase stability or solubility, such as modification of the N-terminal $NH_2$ group or the C terminal COOH group (e.g. modification of the COOH into a $CONH_2$ group).

In the peptides of the present invention comprising a modified redox motif, the motif is located such that, when the epitope fits into the MHC groove, the motif remains outside of the MHC binding groove. The modified redox motif is placed either immediately adjacent to the epitope sequence within the peptide [in other words a linker sequence of zero amino acids between motif and epitope], or is separated from the T cell epitope by a linker comprising an amino acid sequence of amino acids or less. More particularly, the linker comprises 1, 2, 3, 4, or 5 amino acids.

Specific embodiments are peptides with a 0, 1 or 2 amino acid linker between epitope sequence and modified redox motif sequence. In those peptides where the modified redox motif sequence is adjacent to the epitope sequence this is indicated as position P–4 to P–1 or P+1 to P+4 compared to the epitope sequence. Apart from a peptide linker, other organic compounds can be used as linker to link the parts of the peptide to each other (e.g. the modified redox motif sequence to the T cell epitope sequence).

The peptides of the present invention can further comprise additional short amino acid sequences N or C-terminally of the sequence comprising the T cell epitope and the modified redox motif. Such an amino acid sequence is generally referred to herein as a 'flanking sequence'. A flanking sequence can be positioned between the epitope and an endosomal targeting sequence and/or between the modified redox motif and an endosomal targeting sequence. In certain peptides, not comprising an endosomal targeting sequence, a short amino acid sequence may be present N and/or C terminally of the modified redox motif and/or epitope sequence in the peptide. More particularly a flanking sequence is a sequence of between 1 and 7 amino acids, most particularly a sequence of 2 amino acids.

The modified redox motif may be located N-terminal from the epitope.

In certain embodiments of the present invention, peptides are provided comprising one epitope sequence and a modified redox motif sequence. In further particular embodiments, the modified redox motif occurs several times (1, 2, 3, 4 or even more times) in the peptide, for example as repeats of the modified redox motif which can be spaced from each other by one or more amino acids or as repeats which are immediately adjacent to each other. Alternatively, one or more modified redox motifs are provided at both the N and the C terminus of the T cell epitope sequence.

Other variations envisaged for the peptides of the present invention include peptides which contain repeats of a T cell epitope sequence wherein each epitope sequence is preceded and/or followed by the modified redox motif (e.g. repeats of "modified redox motif-epitope" or repeats of "modified redox motif-epitope-modified redox motif"). Herein the modified redox motifs can all have the same sequence but this is not obligatory. It is noted that repetitive sequences of peptides which comprise an epitope which in itself comprises the modified redox motif will also result in a sequence comprising both the 'epitope' and a 'modified redox motif'.

In such peptides, the modified redox motif within one epitope sequence functions as a modified redox motif outside a second epitope sequence.

Typically the peptides of the present invention comprise only one T cell epitope. As described below a T cell epitope in a protein sequence can be identified by functional assays and/or one or more in silica prediction assays. The amino acids in a T cell epitope sequence are numbered according to their position in the binding groove of the MHC proteins. A T-cell epitope present within a peptide consist of between 8 and 25 amino acids, yet more particularly of between 8 and 16 amino acids, yet most particularly consists of 8, 9, 10, 11, 12, 13, 14, 15 or 16 amino acids.

In a more particular embodiment, the T cell epitope consists of a sequence of 9 amino acids. In a further particular embodiment, the T-cell epitope is an epitope, which is presented to T cells by MHC-class II molecules [MHC class II restricted T cell epitopes]. Typically T cell epitope sequence refers to the octapeptide or more specifically nonapeptide sequence which fits into the cleft of an MHC II protein.

The T cell epitope of the peptides of the present invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular, the binding affinity of the modified peptide is no less than 10-fold less than the original peptide, more particularly no less than 5 times less. Peptides of the present invention have a stabilising effect on protein complexes. Accordingly, the stabilising effect of the peptide-MHC complex compensates for the lowered affinity of the modified epitope for the MHC molecule. The sequence comprising the T cell epitope and the reducing compound within the peptide can be further linked to an amino acid sequence (or another organic compound) that facilitates uptake of the peptide into late endosomes for processing and presentation within MHC class II determinants. The late endosome targeting is mediated by signals present in the cytoplasmic tail of proteins and correspond to well-identified peptide motifs. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J. Cell. Biol.* 130, 807-820), the human CD3 gamma protein, the HLA-BM 11 (Copier et al. (1996) *J. Immunol.* 157, 1017-1027), the cytoplasmic tail of the DEC205 receptor (Mahnke et al. (2000) *J. Cell Biol.* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the T cell response towards the antigen. The late endosome targeting sequence can be located either at the amino-terminal or at the carboxy-terminal end of the antigen derived peptide for efficient uptake and processing and can also be coupled through a flanking sequence, such as a peptide sequence of up to 10 amino acids. When using a minor T cell epitope for targeting purpose, the latter is typically located at the amino-terminal end of the antigen derived peptide.

Accordingly, the present invention envisages peptides of antigenic proteins and their use in eliciting specific immune reactions. These peptides can either correspond to fragments of proteins which comprise, within their sequence i.e. a reducing compound and a T cell epitope separated by at most 10, preferably 7 amino acids or less. Alternatively, and for most antigenic proteins, the peptides of the invention are generated by coupling a reducing compound, more particularly a reducing modified redox motif as described herein, N-terminally or C-terminally to a T cell epitope of the antigenic protein (either directly adjacent thereto or with a linker of at most 10, more particularly at most 7 amino acids). Moreover the T cell epitope sequence of the protein and/or the modified redox motif can be modified and/or one or more flanking sequences and/or a targeting sequence can be introduced (or modified), compared to the naturally occurring sequence. Thus, depending on whether or not the features of the present invention can be found within the sequence of the antigenic protein of interest, the peptides of the present invention can comprise a sequence which is 'artificial' or 'naturally occurring'. The peptides of the present invention can vary substantially in length. The length of the peptides can vary from 13 or 14 amino acids, i.e. consisting of an epitope of 8-9 amino acids, adjacent thereto the modified redox motif 5 amino acids with the histidine, up to 20, 25, 30, 40 or 50 amino acids. For example, a peptide may comprise an endosomal targeting sequence of 40 amino acids, a flanking sequence of about 2 amino acids, a motif as described herein of 5 amino acids, a linker of 4 amino acids and a T cell epitope peptide of 9 amino acids.

Accordingly, in particular embodiments, the complete peptide consists of between 13 amino acids up 20, 25, 30, 40, 50, 75 or 100 amino acids. More particularly, where the reducing compound is a modified redox motif as described herein, the length of the (artificial or natural) sequence comprising the epitope and modified redox motif optionally connected by a linker (referred to herein as 'epitope-modified redox motif' sequence), without the endosomal targeting sequence, is critical. The 'epitope-modified redox motif' more particularly has a length of 13, 14, 15, 16, 17, 18 or 19 amino acids. Such peptides of 13 or 14 to 19 amino acids can optionally be coupled to an endosomal targeting signal of which the size is less critical.

As detailed above, in particular embodiments, the peptides of the present invention comprise a reducing modified redox motif as described herein linked to a T cell epitope sequence.

In further particular embodiments, the peptides of the invention are peptides comprising T cell epitopes which do not comprise an amino acid sequence with redox properties within their natural sequence.

However, in alternative embodiments, the T cell epitope may comprise any sequence of amino acids ensuring the binding of the epitope to the MHC cleft. Where an epitope of interest of an antigenic protein comprises a modified redox motif such as described herein within its epitope sequence, the immunogenic peptides according to the present invention comprise the sequence of a modified redox motif as described herein and/or of another reducing sequence coupled N- or C-terminally to the epitope sequence such that (contrary to the modified redox motif present within the epitope, which is buried within the cleft) the attached modified redox motif can ensure the reducing activity.

Accordingly the T cell epitope and motif are immediately adjacent or separated from each other and do not overlap. To assess the concept of "immediately adjacent" or "separated", the 8 or 9 amino acid sequence which fits in the MHC cleft is determined and the distance between this octapeptide or nonapeptide with the redox motif tetrapeptide or modified redox motif pentapeptide including histidine is determined.

Generally, the peptides of the present invention are not natural (thus no fragments of proteins as such) but artificial peptides which contain, in addition to a T cell epitope, a modified redox motif as described herein, whereby the modified redox motif is immediately separated from the T cell epitope by a linker consisting of up to seven, most particularly up to four or up to 2 amino acids.

It has been shown that upon administration (i.e. injection) to a mammal of a peptide according to the invention (or a composition comprising such a peptide), the peptide elicits the activation of T cells recognising the antigen derived T cell epitope and provides an additional signal to the T cell through reduction of surface receptor. This supra-optimal activation results in T cells acquiring cytolytic properties for the cell presenting the T cell epitope, as well as suppressive properties on bystander T cells. In this way, the peptides or composition comprising the peptides described in the present invention, which contain an antigen-derived T cell epitope and, outside the epitope, a modified redox motif can be used for direct immunisation of mammals, including human beings. The invention thus provides peptides of the invention or derivatives thereof, for use as a medicine. Accordingly, the present invention provides therapeutic methods which comprise administering one or more peptides according to the present invention to a patient in need thereof.

The present invention offers methods by which antigen-specific T cells endowed with cytolytic properties can be elicited by immunisation with small peptides. It has been found that peptides which contain (i) a sequence encoding a T cell epitope from an antigen and (ii) a consensus sequence with redox properties, and further optionally also comprising a sequence to facilitate the uptake of the peptide into late endosomes for efficient MHC-class II presentation, elicit suppressor T-cells.

The immunogenic properties of the peptides of the present invention are of particular interest in the treatment and prevention of immune reactions.

Peptides described herein are used as medicament, more particularly used for the manufacture of a medicament for the prevention or treatment of an immune disorder in a mammal, more in particular in a human.

The present invention describes methods of treatment or prevention of an immune disorder of a mammal in need for such treatment or prevention, by using the peptides of the invention, homologues or derivatives thereof, the methods comprising the step of administering to said mammal suffering or at risk of an immune disorder a therapeutically effective amount of the peptides of the invention, homologues or derivatives thereof such as to reduce the symptoms of the immune disorder. The treatment of both humans and animals, such as, pets and farm animals is envisaged. In an embodiment the mammal to be treated is a human. The immune disorders referred to above are in a particular embodiment selected from allergic diseases and autoimmune diseases.

The peptides of the invention or the pharmaceutical composition comprising such as defined herein is preferably administered through sub-cutaneous or intramuscular administration. Preferably, the peptides or pharmaceutical compositions comprising such can be injected sub-cutaneously (SC) in the region of the lateral part of the upper arm, midway between the elbow and the shoulder. When two or more separate injections are needed, they can be administered concomitantly in both arms.

The peptide according to the invention or the pharmaceutical composition comprising such is administered in a therapeutically effective dose. Exemplary but non-limiting dosage regimens are between 50 and 1500 µg, preferably between 100 and 1200 µg. More specific dosage schemes can be between 50 and 250 µg, between 250 and 450 µg or between 850 and 1300 µg, depending on the condition of the patient and severity of disease. Dosage regimen can comprise the administration in a single dose or in 2, 3, 4, 5, or more doses, either simultaneously or consecutively. Exemplary non-limiting administration schemes are the following:

A low dose scheme comprising the SC administration of 50 µg of peptide in two separate injections of 25 µg each (100 µL each) followed by three consecutive injections of 25 µg of peptide as two separate injections of 12.5 µg each (50 µL each).

A medium dose scheme comprising the SC administration of 150 µg of peptide in two separate injections of 75 µg each (300 µL each) followed by three consecutive administrations of 75 µg of peptide as two separate injections of 37.5 µg each (150 µL each).

A high dose scheme comprising the SC administration of 450 µg of peptide in two separate injections of 225 µg each (900 µL each) followed by three consecutive administrations of 225 µg of peptide as two separate injections of 112.5 µg each (450 µL each).

For all the above peptides additional variant are envisaged, wherein between Histidine and Cysteine, one or two amino acids X are present. Typically these external amino acid(s) X is (are) not His, Cys, Ser or Thr.

The peptides of the present invention can also be used in diagnostic in vitro methods for detecting class II restricted CD4+ T cells in a sample. In this method a sample is contacted with a complex of an MHC class II molecule and a peptide according to the present invention. The CD4+ T cells detected by measuring the binding of the complex with cells in the sample, wherein the binding of the complex to a cell is indicative for the presence of CD4+ T cells in the sample.

The complex can be a fusion protein of the peptide and an MHC class II molecule. Alternatively MHC molecules in the complex are tetramers. The complex can be provided as a soluble molecule or can be attached to a carrier.

Accordingly, in particular embodiments, the methods of treatment and prevention of the present invention comprise the administration of an immunogenic peptide as described herein, wherein the peptide comprise a T cell epitope of an antigenic protein which plays a role in the disease to be treated (for instance such as those described above). In further particular embodiments, the epitope used is a dominant epitope.

Peptides in accordance of the present invention will be prepared by synthesising a peptide wherein T cell epitope and modified redox motif will be separated by 0 to 5 amino acids. In certain embodiments the modified redox motif can be obtained by introducing 1, 2 or 3 mutations outside the epitope sequence, to preserve the sequence context as occurring in the protein. Typically amino-acids in P−2 and P−1, as well as in P+10 and P+11, with reference to the nonapeptide which are part of the natural sequence are preserved in the peptide sequence. These flanking residues generally stabilize the binding to MHC class II. In other embodiments the sequence N terminal or C terminal of the epitope will be unrelated to the sequence of the antigenic protein containing the T cell epitope sequence.

Thus based upon the above methods for designing a peptide, a peptide is generated by chemical peptide synthesis, recombinant expression methods or in more exceptional cases, proteolytic or chemical fragmentation of proteins.

Peptides as produced in the above methods can be tested for the presence of a T cell epitope in in vitro and in vivo methods, and can be tested for their reducing activity in in vitro assays. As a final quality control, the peptides can be tested in in vitro assays to verify whether the peptides can generate CD4+ T cells which are cytolytic via an apoptotic pathway for antigen presenting cells presenting the antigen which contains the epitope sequence which is also present in the peptide with the modified redox motif.

The peptides of the present invention can be generated using recombinant DNA techniques, in bacteria, yeast, insect cells, plant cells or mammalian cells. In view of the limited length of the peptides, they can be prepared by chemical peptide synthesis, wherein peptides are prepared by coupling the different amino acids to each other. Chemical synthesis is particularly suitable for the inclusion of e.g.

D-amino acids, amino acids with non-naturally occurring side chains or natural amino acids with modified side chains such as methylated cysteine.

Chemical peptide synthesis methods are well described and peptides can be ordered from companies such as Applied Biosystems and other companies.

Peptide synthesis can be performed as either solid phase peptide synthesis (SPPS) or contrary to solution phase peptide synthesis. The best known SPPS methods are t-Boc and Fmoc solid phase chemistry:

During peptide synthesis several protecting groups are used. For example hydroxyl and carboxyl functionalities are protected by t-butyl group, lysine and tryptophan are protected by t-Boc group, and asparagine, glutamine, cysteine and histidine are protected by trityl group, and arginine is protected by the pbf group. If appropriate, such protecting groups can be left on the peptide after synthesis. Peptides can be linked to each other to form longer peptides using a ligation strategy (chemoselective coupling of two unprotected peptide fragments) as originally described by Kent (Schnelzer & Kent (1992) *Int. J. Pept. Protein Res.* 40, 180-193) and reviewed for example in Tam et al. (2001) *Biopolymers* 60, 194-205 provides the tremendous potential to achieve protein synthesis which is beyond the scope of SPPS. Many proteins with the size of 100-300 residues have been synthesised successfully by this method. Synthetic peptides have continued to play an ever increasing crucial role in the research fields of biochemistry, pharmacology, neurobiology, enzymology and molecular biology because of the enormous advances in the SPPS.

Alternatively, the peptides can be synthesised by using nucleic acid molecules which encode the peptides of this invention in an appropriate expression vector which include the encoding nucleotide sequences. Such DNA molecules may be readily prepared using an automated DNA synthesiser and the well-known codon-amino acid relationship of the genetic code. Such a DNA molecule also may be obtained as genomic DNA or as cDNA using oligonucleotide probes and conventional hybridisation methodologies. Such DNA molecules may be incorporated into expression vectors, including plasmids, which are adapted for the expression of the DNA and production of the polypeptide in a suitable host such as bacterium, e.g. *Escherichia coli*, yeast cell, animal cell or plant cell.

The physical and chemical properties of a peptide of interest (e.g. solubility, stability) are examined to determine whether the peptide is/would be suitable for use in therapeutic compositions. Typically this is optimised by adjusting the sequence of the peptide. Optionally, the peptide can be modified after synthesis (chemical modifications e.g. adding/deleting functional groups) using techniques known in the art.

T cell epitopes on their own are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, the recruitment of additional immune cells to the site, and activation of the B cell cascade leading to production of antibodies. One isotype of these antibodies, IgE, is fundamentally important in the development of allergic symptoms and its production is influenced early in the cascade of events, at the level of the T helper cell, by the nature of the lymphokines secreted. A T cell epitope is the basic element or smallest unit of recognition by a T cell receptor where the epitope comprises amino acid residues essential to receptor recognition, which are contiguous in the amino acid sequence of the protein.

However, upon administration of the peptides with a T-cell epitope and a redox motif, the following events are believed to happen:

activation of antigen (i) specific T cells resulting from cognate interaction with the antigen-derived peptide presented by MHC-class II molecules;

the reductase sequence reduces T cell surface proteins, such as the CD4 molecule, the second domain of which contains a constrained disulfide bridge. This transduces a signal into T cells. Among a series of consequences related to increased oxidative pathway, important events are increased calcium influx and translocation of the NF-kB transcription factor to the nucleus. The latter results in increased transcription of IFN-gamma and granzymes, which allows cells to acquire cytolytic properties via an apoptosis-inducing mechanism; the cytolytic property affects cells presenting the peptide by a mechanism, which involves granzyme B secretion, and Fas-FasL interactions. Since the cell killing effect is obtained via an apoptotic pathway, cytolytic cells is a more appropriate term for these cells than cytotoxic cells.

Destruction of the antigen-presenting target cells prevents activation of other T cells specific for epitopes located on the same antigen, or to an unrelated antigen that would be processed by the same antigen-presenting cell; an additional consequence of T cell activation is to suppress activation of bystander T cells by a cell-cell contact dependent mechanism. In such a case, T cells activated by an antigen presented by a different antigen-presenting cell is also suppressed provided both cytolytic and bystander T cells are in close proximity, namely activated on the surface of the same antigen-presenting cell.

The above-postulated mechanism of action is substantiated with experimental data disclosed in the above cited PCT application WO2008/017517 and publications of the present inventors.

The present invention provides methods for generating antigen-specific cytolytic CD4+ T cells either in vivo or in vitro and, independently thereof, methods to discriminate cytolytic CD4+ T cells from other cell populations such as Foxp3+ Tregs based on characteristic expression data.

The present invention describes in vivo methods for the production of the antigen-specific CD4+ T cells. A particular embodiment relates to the method for producing or isolating the CD4+ T cells by immunising animals (including humans) with the peptides of the invention as described herein and then isolating the CD4+ T cells from the immunised animals. The present invention describes in vitro methods for the production of antigen specific cytolytic CD4+ T cells towards APC. The present invention provides methods for generating antigen specific cytolytic CD4+ T cells towards APC.

In one embodiment, methods are provided which comprise the isolation of peripheral blood cells, the stimulation of the cell population in vitro by an immunogenic peptide according to the invention and the expansion of the stimulated cell population, more particularly in the presence of IL-2. The methods according to the invention have the advantage a high number of CD4+ T cells is produced and that the CD4+ T cells can be generated which are specific for the antigenic protein (by using a peptide comprising an antigen-specific epitope).

In an alternative embodiment, the CD4+ T cells can be generated in vivo, i.e. by the injection of the immunogenic peptides described herein to a subject, and collection of the cytolytic CD4+ T cells generated in vivo.

The antigen-specific cytolytic CD4+ T cells towards APC, obtainable by the methods of the present invention are of particular interest for the administration to mammals for immunotherapy, in the prevention of allergic reactions and the treatment of auto-immune diseases. Both the use of allogenic and autogeneic cells are envisaged.

Cytolytic CD4+ T cells populations are obtained as described herein below.

Antigen-specific cytolytic CD4+ T cells as described herein can be used as a medicament, more particularly for use in adoptive cell therapy, more particularly in the treatment of acute allergic reactions and relapses of autoimmune diseases such as multiple sclerosis. Isolated cytolytic CD4+ T cells or cell populations, more particularly antigen-specific cytolytic CD4+ T cell populations generated as described are used for the manufacture of a medicament for the prevention or treatment of immune disorders. Methods of treatment by using the isolated or generated cytolytic CD4+ T cells are disclosed.

As explained in WO2008/017517 cytolytic CD4+ T cells towards APC can be distinguished from natural Treg cells based on expression characteristics of the cells. More particularly, a cytolytic CD4+ T cell population demonstrates one or more of the following characteristics compared to a natural Treg cell population: an increased expression of surface markers including CD103, CTLA-4, FasI and ICOS upon activation, intermediate expression of CD25, expression of CD4, ICOS, CTLA-4, GITR and low or no expression of CD127 (IL7-R), no expression of CD27.

expression of transcription factor T-bet and egr-2 (Krox-20) but not of the transcription repressor Foxp3, a high production of IFN-gamma and no or only trace amounts of IL-10, IL-4, IL-5, IL-13 or TGF-beta.

Further the cytolytic T cells express CD45RO and/or CD45RA, do not express CCR7, CD27 and present high levels of granzyme B and other granzymes as well as Fas ligand.

The peptides of the invention will, upon administration to a living animal, typically a human being, elicit specific T cells exerting a suppressive activity on bystander T cells.

In specific embodiments the cytolytic cell populations of the present invention are characterised by the expression of FasL and/or Interferon gamma. In specific embodiments the cytolytic cell populations of the present invention are further characterised by the expression of GranzymeB.

This mechanism also implies and the experimental results show that the peptides of the invention, although comprising a specific T-cell epitope of a certain antigen, can be used for the prevention or treatment of disorders elicited by an immune reaction against other T-cell epitopes of the same antigen or in certain circumstances even for the treatment of disorders elicited by an immune reaction against other T-cell epitopes of other different antigens if they would be presented through the same mechanism by MHC class II molecules in the vicinity of T cells activated by peptides of the invention.

Isolated cell populations of the cell type having the characteristics described above, which, in addition are antigen-specific, i.e. capable of suppressing an antigen-specific immune response are disclosed.

The present invention provides pharmaceutical compositions comprising one or more peptides according to the present invention, further comprising a pharmaceutically acceptable carrier. As detailed above, the present invention also relates to the compositions for use as a medicine or to methods of treating a mammal of an immune disorder by using the composition and to the use of the compositions for the manufacture of a medicament for the prevention or treatment of immune disorders. The pharmaceutical composition could for example be a vaccine suitable for treating or preventing immune disorders, especially airborne and foodborne allergy, as well as diseases of allergic origin. As an example described further herein of a pharmaceutical composition, a peptide according to the invention is adsorbed on an adjuvant suitable for administration to mammals, such as aluminium hydroxide (alum). Typically, 50 µg of the peptide adsorbed on alum are injected by the subcutaneous route on 3 occasions at an interval of 2 weeks. It should be obvious for those skilled in the art that other routes of administration are possible, including oral, intra-nasal or intramuscular. Also, the number of injections and the amount injected can vary depending on the conditions to be treated. Further, other adjuvants than alum can be used, provided they facilitate peptide presentation in MHC-class II presentation and T cell activation. Thus, while it is possible for the active ingredients to be administered alone, they typically are presented as pharmaceutical formulations. The formulations, both for veterinary and for human use, of the present invention comprise at least one active ingredient, as above described, together with one or more pharmaceutically acceptable carriers. The present invention relates to pharmaceutical compositions, comprising, as an active ingredient, one or more peptides according to the invention, in admixture with a pharmaceutically acceptable carrier. The pharmaceutical composition of the present invention should comprise a therapeutically effective amount of the active ingredient, such as indicated hereinafter in respect to the method of treatment or prevention. Optionally, the composition further comprises other therapeutic ingredients. Suitable other therapeutic ingredients, as well as their usual dosage depending on the class to which they belong, are well known to those skilled in the art and can be selected from other known drugs used to treat immune disorders.

The term "pharmaceutically acceptable carrier" as used herein means any material or substance with which the active ingredient is formulated in order to facilitate its application or dissemination to the locus to be treated, for instance by dissolving, dispersing or diffusing the composition, and/or to facilitate its storage, transport or handling without impairing its effectiveness. They include any and all solvents, dispersion media, coatings, antibacterial and anti-fungal agents (for example phenol, sorbic acid, chlorobutanol), isotonic agents (such as sugars or sodium chloride) and the like. Additional ingredients may be included in order to control the duration of action of the immunogenic peptide in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in the pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives typically contain 8 to 22 carbon atoms. Examples of alkylarylsulphonates are the sodium, calcium or alcanolamine salts of dodecyl benzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidyl-ethanolamine, phosphatidylserine, phosphatidylglycerine, lysolecithin, cardio lipin, dioctanylphosphatidylcholine, dipalmitoylphoshatidylcholine and their mixtures.

Suitable non-ionic surfactants include polyethoxylated and poly propoxylated derivatives of alkyl phenols, fatty alcohols, fatty acids, aliphatic amines or amides containing at least 12 carbon atoms in the molecule, alkylarene sulphonates and dialkylsulphosuccinates, such as polyglycol ether derivatives of aliphatic and cycloaliphatic alcohols, saturated and unsaturated fatty acids and alkylphenols, the derivatives typically containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants. Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbucw', 2 d ed. (Hanser Verlag, Vienna, 1981) and "Encyclopaedia of Surfactants, (Chemical Publishing Co., New York, 1981). Peptides, homologues or derivatives thereof according to the invention (and their physiologically acceptable salts or pharmaceutical compositions all included in the term "active ingredients") may be administered by any route appropriate to the condition to be treated and appropriate for the compounds, here the proteins and fragments to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intra-arterial, intrathecal and epidural). The preferred route of administration may vary with for example the condition of the recipient or with the diseases to be treated. As described herein, the carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intraarterial, intrathecal and epidural) administration.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Typical unit dosage formulations are those containing a daily dose or unit daily sub-dose, as herein above recited, or an appropriate fraction thereof, of an active ingredient. It should be understood that in addition to the ingredients particularly mentioned above the formulations of this invention may include other agents conventional in the art having regard to the type of formulation in question, for example those suitable for oral administration may include flavouring agents. Peptides, homologues or derivatives thereof according to the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injection include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof. In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Cytolytic CD4+ T cells as obtained in the present invention, induce APC apoptosis after MHC-class II dependent cognate activation, affecting both dendritic and B cells, as demonstrated in vitro and in vivo, and (2) suppress bystander T cells by a contact-dependent mechanism in the absence of IL-10 and/or TGF-beta. Cytolytic CD4+ T cells can be distinguished from both natural and adaptive Tregs, as discussed in detail in WO2008/017517.

The present invention will now be illustrated by means of the following examples which are provided without any limiting intention. Furthermore, all references described herein are explicitly included herein by reference.

EXAMPLES

Example 1: Peptide Design

Compared to the peptide disclosed in WO2016059236 a peptide is synthesised comprising a T cell epitope of the C domain of insulin wherein the VR dipeptide sequence, which does not occur in the sequence of Insulin has been removed, as shown in the alignment depicted below:

```
P17 001:
                                      [SEQ ID NO: 25]
        HCPYC VR SLQPLALEGSLQKRG

P17 003:
                                      [SEQ ID NO: 26]
        HCPYC-   SLQPLALEGSLQKRG
```

The P17 003 peptide thus contains a CxxC [SEQ ID NO:18] motif preceded by His wherein xx are Pro and Tyr. The T cell epitope of 9 amino acids has the sequence LALEGSLQK [SEQ ID NO: 3] and is separated from the CxxC [SEQ ID NO:18] motif by a linker of 4 amino acids SLQP [residues 1 to 4 of SEQ ID NO: 20]. The RG dipeptide is a flanking sequence c terminal of the epitope. In this peptide the sequence SLQPLALEGSLQKRG [SEQ ID NO: 20] is 100% identical to the sequence as occurring in insulin.

Example 2: Methodology to Assess Reducing Activity of Peptides

The reductase activity of the peptides is determined using a fluorescent described in Tomazzolli et al. (2006) Anal. Biochem. 350, 105-112. Two peptides with a FITC label become self-quenching when they covalently attached to each other via a disulfide bridge. Upon reduction by a peptide in accordance with the present invention, the reduced individual peptides become fluorescent again.

Control experiments were performed with dithiothreitol (100% reducing activity) and water (100% reducing activity).

The peptide P17 001 showed 68% reducing activity, whereas the peptide P17 003 showed 65% reducing activity.

Example 3: Interferon Gamma Release by Cytolytic CD4+ T Cell Lines

Interferon gamma is an important marker to characterise cytolytic CD4+ T cells. A specific CD4+ T cell line was obtained by priming and stimulating naïve CD4+ T cells from a T1D patient (T1D07) with peptide p17-001. After 12 stimulations, cells were co-cultured with autologous LCL B cells loaded (2 μM) with peptide p17-001 or p17-003. After 24 hours, supernatants were collected and IFN-gamma was measured by multiplex assay (see table 1 below).

TABLE 1

|          | Stimulus 1 IFN-gamma (pg/ml) |
| --- | --- |
| p17 UL   | 2.35 ± 1.2  |
| p17 001  | 11.1 ± 0.8  |
| p17 003  | 29.7 ± 14.1 |

There is a striking difference in IFN-gamma production between the two peptides (about 3 times more IFN-gamma produced after stimulation with p17 003 compared to p17 001).

Example 4: FasL Release by Cytolytic CD4+ T Cell Lines

The T cell line originally generated with p17 001 as described in example 3 above was divided and stimulated with peptide P17 003 or P17 001 over 4 successive in vitro stimulations using autologous LCL B cell line as APC. At day 11 of every stimulation (total of 4), cells were tested for FasL after restimulation with their corresponding peptide presented by autologous B cells. Supernatants were collected after 24 h (stimulation 1 and 2) or 72 h (stimulation 3 and 4) of co-culture.

TABLE 2

FasL expression by CD4+ T cell lines from T1D patients

| FasL expression (pg/ml) | Stimulation 1 | Stimulation 2 | Stimulation 3 | Stimulation 4 |
|---|---|---|---|---|
| Control | 0 | 0 | 0 | 0 |
| P17-001 | 1335 ± 23.1 | 1144 ± 15.4 | 1227 ± 49.1 | 1008 ± 102 |
| P17-003 | 1795 ± 42.4 | 1812 ± 34.7 | 2063 ± 166 | 1526 ± 102 |

FasL (also named sFasL) expression is significantly higher for P17-003 for each of the four stimulations.

This illustrates a greater capacity of the P17-003 peptide to generate cytolytic T cells compared to the P17-001 peptide.

Example 5: Release of sFasL and Cytokine Production in T1D-Patients PBMCs

PBMCs from T1D-patient T1D018 were stimulated in vitro either with P17001 peptide or P17003 peptide. These two populations specifically release 11-5 after antigenic activation. After 6 stimulation cycles with the peptides, both cell lines were enriched for IL-5 producing cells with cytokine capture beads. The two populations of Interleukin-5 negative cells were used as controls.

These four populations are then tested for specific release of sFasL, Granzyme B and cytokines after stimulation with their cognate peptide (P17-001 or P17-003). Supernatants are collected after 24 h of culture and sFasL and Granzyme B are measured by ELISA (sFasL: Diaclone 851730010; Granzyme B: eBioscience BMS2027) and cytokines by MACSplex Cytokine 12 kit (Miltenyi, 130-099-169).

5.1. sFasL Production sFasL levels of the four cell lines are shown in FIG. 1. This shows that IL5 positive fractions (black histograms) which are enriched in specific cells specific for peptide p17-003 or p17-001 release more sFasL compared to the negative fractions (open histograms), indication of an efficient specific cell purification.

Moreover, results indicate that cells generated by in vitro stimulation with p17-003 specifically release significantly 4.5 fold more sFasL compared with cells generated by peptide p17-001 (p<0,0001).

5.2. Granzyme B Production

IL5 positive fractions which are enriched in specific cells specific for peptide p17-003 or p17-001 are tested for release of more Granzyme B compared to the IL5 negative fractions, as a measure of efficient specific cell purification.

Moreover, cells generated by in vitro stimulation with p17-003 will be tested for specifically increased release of Granzyme B as compared with cells generated by peptide p17-001.

5.3. Cytokine Release

To determine if the in vitro cultured cells from T1D donors are specific for peptide P17001 or P17003, the release of cytokines, a hallmark for cell activation upon peptide stimulation, was investigated using MACSplex Cytokine 12 kit (Miltenyi, 130-099-169). Supernatant was collected after 24 h from the culture of T1D donor PBMCs in the absence or presence of the peptide. Cytokine concentrations were determined for the biological duplicates and displayed in pg/mL. Specificity test was performed at the end of stimulation 10 (resting day). The result is presented as the difference in concentration of each cytokine in the condition without and with peptide.

Figure 2:
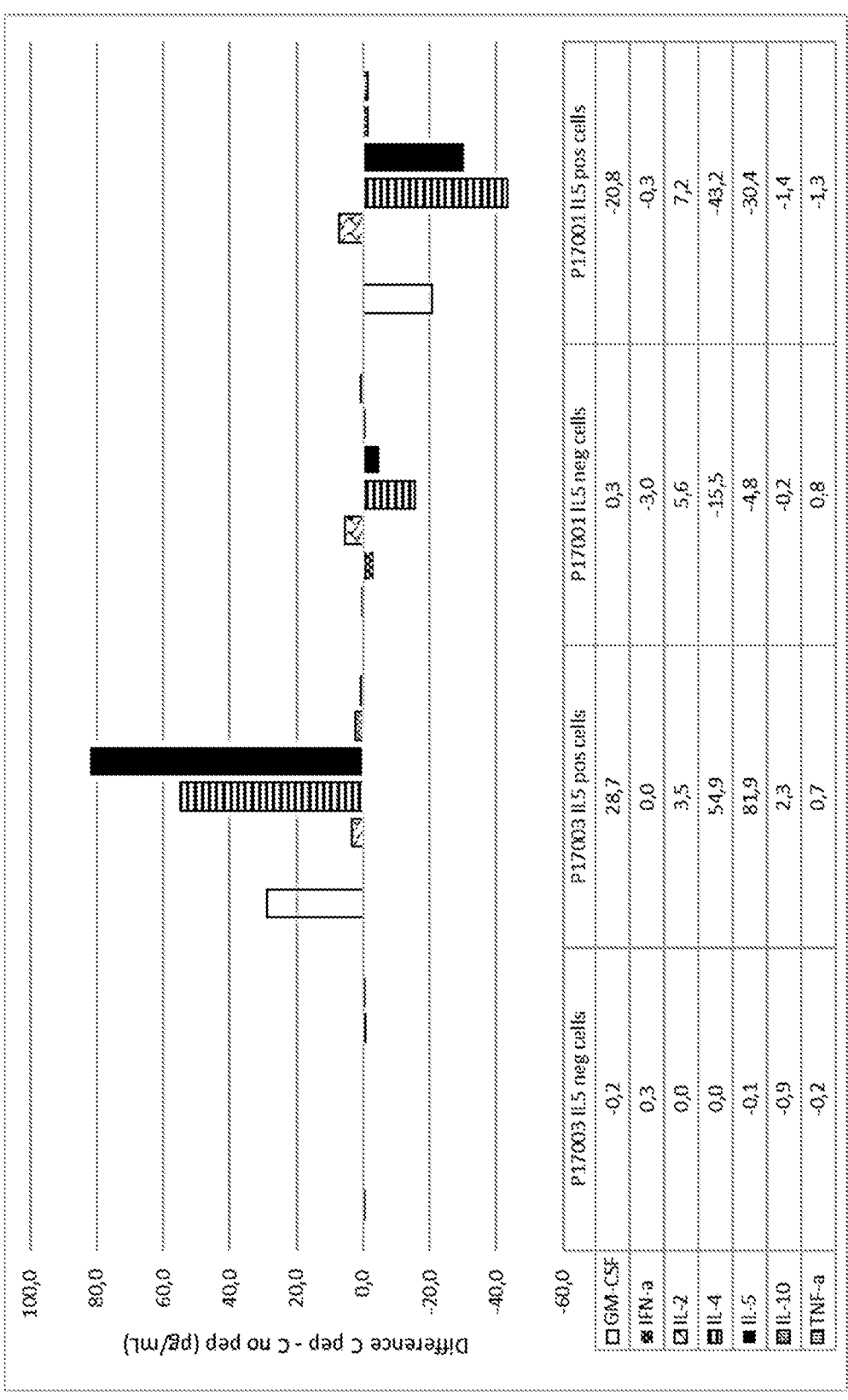
FIG. 2: This figure shows the response of cell lines to stimulation by p17-003 or p17-001 in terms of cytokines production.

FIG. 2 shows that IL5 positive fraction of P17003 cell line responds specifically to stimulation compared to the cell lines P17003 IL5 negative, P17001 IL5 negative and P17001 IL5 positive. This illustrates that peptide P17003 is more potent in eliciting peptide specific cells compared with P17001.

In conclusion, cells generated de novo with P17-003 are more potent at releasing lytic molecules (such as sFasL and potentially Granzyme B) and cytokines than cells generated with P17-001. The peptide thus results in a CD4+ cell population with superior cytolytic properties against APC presenting insulin epitopes.

Example 6: Clinical Trial

Prior to administration, the peptide of the invention is reconstituted with the diluent containing the adjuvant. The product should be reconstituted extemporaneously and is preferably used within less than 3 hours after reconstitution.

The investigational medicinal product can be formulated so that after reconstitution in the diluent, the concentration of the peptide in the vial is 250 μg/ml. The appropriate volume will be withdrawn to comply with the clinical trial protocol. For example:

The low dose (Cohort 1) can comprise the SC administration of 50 μg of peptide in two separate injections of 25 μg each (100 μL each) followed by three consecutive injections of 25 μg of peptide as two separate injections of 12.5 μg each (50 μL each).

The medium dose (Cohort 2) can comprise the SC administration of 150 μg of peptide in two separate injections of 75 μg each (300 μL each) followed by three consecutive administrations of 75 μg of peptide as two separate injections of 37.5 μg each (150 μL each).

The higher dose (Cohort 3) can comprise the SC administration of 450 μg of peptide in two separate injections of 225 μg each (900 μL each) followed by three consecutive administrations of 225 μg of peptide as two separate injections of 112.5 μg each (450 μL each).

Investigational products according to the invention are preferably injected subcutaneously (SC) in the region of the lateral part of the upper arm, midway between the elbow and the shoulder. When two separate injections are needed, they are preferably administered concomitantly in both arms: e.g. injection 1 in the right arm and injection 2 in the left arm.

SEQUENCES redox motif

SEQ ID NO: 1

MISC_FEATURE: (2) . . . (3) Xaa can be any amino acid
MISC_FEATURE: (4) . . . (4) Xaa is Cys, Ser or Thr
Cys Xaa Xaa Xaa -continued

| SEQUENCES |
| --- |

```
redox motif
                                                     SEQ ID NO: 2
MISC_FEATURE: (1) . . . (1) Xaa is Cys, Ser or Thr
MISC_FEATURE: (2) . . . (3) Xaa can be any amino acid
Xaa Xaa Xaa Cys insulin epitope
                                                     SEQ ID NO: 3
Leu Ala Leu Glu Gly Ser Leu Gln Lys redox motif + insulin epitope
                                                     SEQ ID NO: 4
MISC_FEATURE: (2) . . . (3) Xaa can be any amino acid
MISC_FEATURE: (4) . . . (4) Xaa is Cys, Ser or Thr
Cys Xaa Xaa Xaa Ser Leu Gln Pro Leu Ala Leu Glu Gly Ser Leu Gln Lys redox motif + insulin epitope
                                                     SEQ ID NO: 5
MISC_FEATURE: (1) . . . (1) Xaa is Cys, Ser or Thr
MISC_FEATURE: (2) . . . (3) Xaa can be any amino acid
Xaa Xaa Xaa Cys Ser Leu Gln Pro Leu Ala Leu Glu Gly Ser Leu Gln Lys redox motif + insulin epitope
                                                     SEQ ID NO: 6
MISC_FEATURE: (2) . . . (3) Xaa can be any amino acid
Cys Xaa Xaa Cys Ser Leu Gln Pro Leu Ala Leu Glu Gly Ser Leu Gln Lys redox motif + T cell epitope
                                                     SEQ ID NO: 7
MISC_FEATURE: (3) . . . (4) Xaa can be any amino acid
MISC_FEATURE: (5) . . . (5) Xaa is Cys, Ser or Thr
His Cys Xaa Xaa Xaa Ser Leu Gln Pro Leu Ala Leu Glu Gly Ser Leu Gln Lys redox motif + T cell epitope
                                                     SEQ ID NO: 8
MISC_FEATURE: (2) . . . (2) Xaa is Cys, Ser or Thr
MISC_FEATURE: (3) . . . (4) Xaa can be any amino acid
His Xaa Xaa Xaa Cys Ser Leu Gln Pro Leu Ala Leu Glu Gly Ser Leu Gln Lys redox motif + insulin T cell epitope
                                                     SEQ ID NO: 9
MISC_FEATURE: (3) . . . (4) Xaa can be any any amino acid
His Cys Xaa Xaa Cys Ser Leu Gln Pro Leu Ala Leu Glu Gly Ser Leu Gln Lys redoc motif + insulin epitope
                                                     SEQ ID NO: 10
MISC_FEATURE: (2) . . . (3) Xaa can be any amino acid
MISC_FEATURE: (4) . . . (4) Xaa is Cys, Ser or Thr
Cys Xaa Xaa Xaa Leu Gln Pro Leu Ala Leu Glu Gly Ser Leu Gln Lys Arg Gly redox motif + insulin T cell epitope
                                                     SEQ ID NO: 11
MISC_FEATURE: (1) . . . (1) Xaa is Cys, Ser or Thr
MISC_FEATURE: (2) . . . (2) Xaa can be any amino acid
MISC_FEATURE: (2) . . . (3) Xaa can be any amino acid
Xaa Xaa Xaa Cys Ser Leu Gln Pro Leu Ala Leu Glu Gly Ser Leu Gln Lys Arg Gly Redox motif + insulin T cell epitope
                                                     SEQ ID NO: 12
MISC_FEATURE: (2) . . . (3) Xaa can be any amino acid
Cys Xaa Xaa Cys Ser Leu Gln Pro Leu Ala Leu Glu Gly Ser Leu Gln Lys Arg Gly redox motif + insulin T cell epitope
                                                     SEQ ID NO: 13
MISC_FEATURE: (3) . . . (4) Xaa can be any amino amino acid
MISC_FEATURE: (5) . . . (5) Xaa is Cys, Ser or Thr
His Cys Xaa Xaa Xaa Ser Leu Gln Pro Leu Ala Leu Glu Gly Ser Leu Gln Lys Arg Gly redox motif + insulin T cell epitope
                                                     SEQ ID NO: 14
MISC_FEATURE: (2) . . . (2) Xaa is Cys, Ser or Thr
MISC_FEATURE: (3) . . . (4) Xaa can be any amino acid
His Xaa Xaa Xaa Cys Ser Leu Gln Pro Leu Ala Leu Glu Gly Ser Leu Gln Lys Arg Gly
```

-continued

---

SEQUENCES

--- redox motif + insulin T cell epitope
                                                                                    SEQ ID NO: 15
MISC_FEATURE: (3) . . . (4) Xaa can be any amino acid
His Cys Xaa Xaa Cys Ser Leu Gln Pro Leu Ala Leu Glu Gly Ser Leu Gln Lys Arg Gly redox motif
                                                                                    SEQ ID NO: 16
MISC_FEATURE: (4) . . . (4) Xaa is Cys, Ser or Thr
Cys Pro Tyr Xaa redox motif
                                                                                    SEQ ID NO: 17
MISC_FEATURE: (1) . . . (1) Xaa is Cys, Ser or Thr
Xaa Pro Tyr Cys redox motif
                                                                                    SEQ ID NO: 18
MISC_FEATURE: (2) . . . (3) Xaa can be any amino acid
Cys Xaa Xaa Cys redox motif
                                                                                    SEQ ID NO: 19
Cys Pro Tyr Cys peptide comprising insulin T cell epitope
                                                                                    SEQ ID NO: 20
Ser Leu Gln Pro Leu Ala Leu Glu Gly Ser Leu Gln Lys Arg Gly redox motif
                                                                                    SEQ ID NO: 21
MISC_FEATURE: (2) . . . (3) Xaa can be any amino acid
Ser Xaa Xaa Cys redox motif
                                                                                    SEQ ID NO: 22
MISC_FEATURE: (2) . . . (3) Xaa can be any amino acid
Thr Xaa Xaa Cys redox motif
                                                                                    SEQ ID NO: 23
MISC_FEATURE: (2) . . . (3) CXXS
Cys Xaa Xaa Ser redox motif
                                                                                    SEQ ID NO: 24
MISC_FEATURE: (2) . . . (3) Xaa can be any amino acid
Cys Xaa Xaa Thr peptide with redox motif and insulin T cell epitope
                                                                                    SEQ ID NO: 25
His Cys Pro Tyr Cys Val Arg Ser Leu Gln Pro Leu Ala Leu Glu Gly Ser Leu Gln Lys Arg Gly peptide with redox motif and insulin T cell epitope
                                                                                    SEQ ID NO: 26
His Cys Pro Tyr Cys Ser Leu Gln Pro Leu Ala Leu Glu Gly Ser Leu Gln Lys Arg Gly

---

SEQUENCE LISTING

---

Sequence total quantity: 26
SEQ ID NO: 1              moltype =   length =
SEQUENCE: 1
000

SEQ ID NO: 2              moltype =   length =
SEQUENCE: 2
000

SEQ ID NO: 3              moltype = AA  length = 9
FEATURE                  Location/Qualifiers
REGION                   1..9
                         note = insulin epitope

```
source                  1..9
                        mol_type = protein
                        organism = synthetic construct
SEQUENCE: 3
LALEGSLQK                                                                    9

SEQ ID NO: 4            moltype = AA  length = 17
FEATURE                 Location/Qualifiers
REGION                  1..17
                        note = redox motif + insulin epitope
VARIANT                 2..3
                        note = Xaa can be any amino acid
VARIANT                 4
                        note = Xaa is Cys, Ser or Thr
source                  1..17
                        mol_type = protein
                        organism = synthetic construct
SEQUENCE: 4
CXXXSLQPLA LEGSLQK                                                          17

SEQ ID NO: 5            moltype = AA  length = 17
FEATURE                 Location/Qualifiers
REGION                  1..17
                        note = redox motif + insulin epitope
VARIANT                 1
                        note = Xaa is Cys, Ser or Thr
VARIANT                 2..3
                        note = Xaa can be any amino acid
source                  1..17
                        mol_type = protein
                        organism = synthetic construct
SEQUENCE: 5
XXXCSLQPLA LEGSLQK                                                          17

SEQ ID NO: 6            moltype = AA  length = 17
FEATURE                 Location/Qualifiers
REGION                  1..17
                        note = redox motif + insulin epitope
VARIANT                 2..3
                        note = Xaa can be any amino acid
source                  1..17
                        mol_type = protein
                        organism = synthetic construct
SEQUENCE: 6
CXXCSLQPLA LEGSLQK                                                          17

SEQ ID NO: 7            moltype = AA  length = 18
FEATURE                 Location/Qualifiers
REGION                  1..18
                        note = redox motif + T cell epitope
VARIANT                 3..4
                        note = Xaa can be any amino acid
VARIANT                 5
                        note = Xaa is Cys, Ser or Thr
source                  1..18
                        mol_type = protein
                        organism = synthetic construct
SEQUENCE: 7
HCXXXSLQPL ALEGSLQK                                                         18

SEQ ID NO: 8            moltype = AA  length = 18
FEATURE                 Location/Qualifiers
REGION                  1..18
                        note = redox motif + T cell epitope
VARIANT                 2
                        note = Xaa is Cys, Ser or Thr
VARIANT                 3..4
                        note = Xaa can be any amino acid
source                  1..18
                        mol_type = protein
                        organism = synthetic construct
SEQUENCE: 8
HXXXCSLQPL ALEGSLQK                                                         18

SEQ ID NO: 9            moltype = AA  length = 18
FEATURE                 Location/Qualifiers
REGION                  1..18
                        note = redox motif + insulin T cell epitope
VARIANT                 3..4
```

-continued

```
                          note = Xaa can be any any amino acid
source                    1..18
                          mol_type = protein
                          organism = synthetic construct
SEQUENCE: 9
HCXXCSLQPL ALEGSLQK                                                18

SEQ ID NO: 10             moltype = AA  length = 18
FEATURE                   Location/Qualifiers
REGION                    1..18
                          note = redoc motif + insulin epitope
VARIANT                   2..3
                          note = Xaa can be any amino acid
VARIANT                   4
                          note = Xaa is Cys, Ser or Thr
source                    1..18
                          mol_type = protein
                          organism = synthetic construct
SEQUENCE: 10
CXXXLQPLAL EGSLQKRG                                                18

SEQ ID NO: 11             moltype = AA  length = 19
FEATURE                   Location/Qualifiers
REGION                    1..19
                          note = redox motif + insulin T cell epitope
VARIANT                   1
                          note = Xaa is Cys, Ser or Thr
VARIANT                   2..3
                          note = Xaa can be any amino acid
source                    1..19
                          mol_type = protein
                          organism = synthetic construct
SEQUENCE: 11
XXXCSLQPLA LEGSLQKRG                                               19

SEQ ID NO: 12             moltype = AA  length = 19
FEATURE                   Location/Qualifiers
REGION                    1..19
                          note = Redox motif + insulin T cell epitope
VARIANT                   2..3
                          note = Xaa can be any amino acid
source                    1..19
                          mol_type = protein
                          organism = synthetic construct
SEQUENCE: 12
CXXCSLQPLA LEGSLQKRG                                               19

SEQ ID NO: 13             moltype = AA  length = 20
FEATURE                   Location/Qualifiers
REGION                    1..20
                          note = redox motif + insulin T cell epitope
VARIANT                   3..4
                          note = Xaa can be any amino acid
VARIANT                   5
                          note = Xaa is Cys, Ser or Thr
source                    1..20
                          mol_type = protein
                          organism = synthetic construct
SEQUENCE: 13
HCXXXSLQPL ALEGSLQKRG                                              20

SEQ ID NO: 14             moltype = AA  length = 20
FEATURE                   Location/Qualifiers
REGION                    1..20
                          note = redox motif + insulin T cell epitope
VARIANT                   2
                          note = Xaa is Cys, Ser or Thr
VARIANT                   3..4
                          note = Xaa can be any amino acid
source                    1..20
                          mol_type = protein
                          organism = synthetic construct
SEQUENCE: 14
HXXXCSLQPL ALEGSLQKRG                                              20

SEQ ID NO: 15             moltype = AA  length = 20
FEATURE                   Location/Qualifiers
REGION                    1..20
                          note = redoX motif + insulin T cell epitope
```

-continued

```
VARIANT                 3..4
                        note = Xaa can be any amino acid
source                  1..20
                        mol_type = protein
                        organism = synthetic construct
SEQUENCE: 15
HCXXCSLQPL ALEGSLQKRG                                          20

SEQ ID NO: 16           moltype =   length =
SEQUENCE: 16
000

SEQ ID NO: 17           moltype =   length =
SEQUENCE: 17
000

SEQ ID NO: 18           moltype =   length =
SEQUENCE: 18
000

SEQ ID NO: 19           moltype = AA   length = 4
FEATURE                 Location/Qualifiers
REGION                  1..4
                        note = redox motif
source                  1..4
                        mol_type = protein
                        organism = synthetic construct
SEQUENCE: 19
CPYC                                                            4

SEQ ID NO: 20           moltype = AA   length = 15
FEATURE                 Location/Qualifiers
REGION                  1..15
                        note = peptide comprising insulin T cell epitope
source                  1..15
                        mol_type = protein
                        organism = synthetic construct
SEQUENCE: 20
SLQPLALEGS LQKRG                                               15

SEQ ID NO: 21           moltype =   length =
SEQUENCE: 21
000

SEQ ID NO: 22           moltype =   length =
SEQUENCE: 22
000

SEQ ID NO: 23           moltype =   length =
SEQUENCE: 23
000

SEQ ID NO: 24           moltype =   length =
SEQUENCE: 24
000

SEQ ID NO: 25           moltype = AA   length = 22
FEATURE                 Location/Qualifiers
REGION                  1..22
                        note = peptide with redox motif and insulin T cell epitope
source                  1..22
                        mol_type = protein
                        organism = synthetic construct
SEQUENCE: 25
HCPYCVRSLQ PLALEGSLQK RG                                       22

SEQ ID NO: 26           moltype = AA   length = 20
FEATURE                 Location/Qualifiers
REGION                  1..20
                        note = peptide with redox motif and insulin T cell epitope
source                  1..20
                        mol_type = protein
                        organism = synthetic construct
SEQUENCE: 26
HCPYCSLQPL ALEGSLQKRG                                          20
```

The invention claimed is:

1. An in vitro method for the generation of a population of cytolytic CD4+ T cells against antigen presenting cells (APC) presenting insulin epitopes, comprising the steps of:

providing peripheral blood cells;

contacting said cells in vitro with an isolated immunogenic peptide comprising the amino acid sequence of HCXX[CST]SLQPLALEGSLQK [SEQ ID NO:7] or H[CST]XXCSLQPLALEGSLQK [SEQ ID NO:8] wherein X stands for any amino acid, and wherein the peptide has a length of between 12 and 50 amino acids; and expanding said cells in the presence of IL-2.

2. A pharmaceutical composition comprising (i) an immunogenic peptide comprising the amino acid sequence HCXX[CST]SLQPLALEGSLQK [SEQ ID NO: 7] or H[CST]XXCSLQPLALEGSLQK [SEQ ID NO:8] and (ii) a pharmaceutically acceptable carrier, wherein X stands for any amino acid, the immunogenic peptide has a length of between 12 and 50 amino acids, and the pharmaceutical composition is suitable for subcutaneous administration.

3. The pharmaceutical composition according to claim 2, wherein the immunogenic peptide comprises the amino acid sequence HCXXCSLQPLALEGSLQK [SEQ ID NO: 9], wherein X stands for any amino acid.

4. The pharmaceutical composition according to claim 2, wherein the immunogenic peptide consists of the amino acid sequence HCPYCSLQPLALEGSLQKRG [SEQ ID NO: 26].

5. The pharmaceutical composition according to claim 2, wherein the immunogenic peptide consists of the amino acid sequence HCXX[CST]SLQPLALEGSLQK [SEQ ID NO:7] or H[CST]XXCSLQPLALEGSLQK [SEQ ID NO:8], wherein X stands for any amino acid.

6. The pharmaceutical composition according to claim 2, wherein the immunogenic peptide consists of the amino acid sequence HCXXCSLQPLALEGSLQK [SEQ ID NO: 9], wherein X stands for any amino acid.

7. A method of treating type 1 diabetes comprising subcutaneously administering to a subject in need thereof a therapeutically sufficient amount of an immunogenic peptide comprising the amino acid sequence of HCXX[CST]SLQPLALEGSLQK [SEQ ID NO:7] or H[CST]XXCSLQPLALEGSLQK [SEQ ID NO:8], wherein X stands for any amino acid, and wherein the peptide has a length of between 12 and 50 amino acids.

8. The method of claim 7, wherein the amino acid sequence comprises HCXXCSLQPLALEGSLQK [SEQ ID NO: 9], wherein X stands for any amino acid.

9. The method of claim 7, wherein the amino acid sequence consists of HCPYCSLQPLALEGSLQKRG [SEQ ID NO: 26].

10. The method of claim 7, wherein the amino acid sequence consists of HCXX[CST]SLQPLALEGSLQK [SEQ ID NO:7] or H[CST]XXCSLQPLALEGSLQK [SEQ ID NO:8], wherein X stands for any amino acid.

11. The method of claim 7, wherein the amino acid sequence consists of HCXXCSLQPLALEGSLQK [SEQ ID NO: 9], wherein X stands for any amino acid.

* * * * *